(12) United States Patent
Thummisi et al.

(10) Patent No.: US 11,271,938 B1
(45) Date of Patent: Mar. 8, 2022

(54) SYSTEM AND METHOD FOR DIRECTIVES BASED MECHANISM TO ORCHESTRATE SECURE COMMUNICATIONS IN MULTI-CLOUD DISTRIBUTED SYSTEMS

(71) Applicant: Raghunathvenkata Ramana Thummisi, Saratoga, CA (US)

(72) Inventors: Raghunathvenkata Ramana Thummisi, Saratoga, CA (US); Roopa Nagaraju, Saratoga, CA (US)

(73) Assignee: Raghunathvenkata Ramana Thummisi

( * ) Notice: Subject to any disclaimer, the term of this patent is extended or adjusted under 35 U.S.C. 154(b) by 0 days.

(21) Appl. No.: 17/380,974

(22) Filed: Jul. 20, 2021

(51) Int. Cl.
*H04L 29/06* (2006.01)
*G16H 10/60* (2018.01)

(52) U.S. Cl.
CPC .......... *H04L 63/101* (2013.01); *G16H 10/60* (2018.01); *H04L 63/104* (2013.01); *H04L 63/20* (2013.01)

(58) Field of Classification Search
CPC ..... H04L 63/101; H04L 63/104; H04L 63/20; G16H 10/60
See application file for complete search history.

(56) References Cited

U.S. PATENT DOCUMENTS

| | | | | |
|---|---|---|---|---|
| 9,805,213 | B1* | 10/2017 | Kragh | H04L 63/0861 |
| 10,778,775 | B2* | 9/2020 | Lear | H04L 63/20 |
| 2007/0150315 | A1* | 6/2007 | Bennett | G06F 21/6245 705/3 |
| 2014/0075498 | A1* | 3/2014 | Porras | H04L 63/107 726/1 |
| 2015/0012315 | A1* | 1/2015 | Mohammad | G06F 21/00 705/7.11 |
| 2017/0223005 | A1* | 8/2017 | Birgisson | H04L 63/0807 |
| 2017/0302531 | A1* | 10/2017 | Maes | H04L 67/10 |

* cited by examiner

*Primary Examiner* — Yonas A Bayou
(74) *Attorney, Agent, or Firm* — DLA Piper, LLP (US)

(57) ABSTRACT

A directive based access system and method manage access permissions in systems. In one embodiment, the directive based access system and method may be used to orchestrate effective secure access control and communications in multi-cloud distributed systems. In one implementation, the directive based access system and method may include a lineage traceability enforcement engine that uses a lineage traceability. The directive based access system and method may also be implemented using other mechanisms such as blockchain based Hyperledger based system.

18 Claims, 15 Drawing Sheets

Directive Access Dictionary

324

| Security Directives | WHY? (Context) | Which files/repositoryAccess allowed? | Expiration (hours/days/months/years/unlimited) | Can share access permissions with users (#) | Total Access attempts | Number of access attempts/hour/day/week/month/year | Read/Write/Delete/Create/Terminate (Y/N) | Write (Y/N) | Delete (Y/N) | Geo locations allowed | Download access (Y/N) | Time of access |
|---|---|---|---|---|---|---|---|---|---|---|---|---|
| 1 to N | Situational Privilege of User (1 to M) enabling alignment with the Directive 1 | 1 to R | | | | | | | | | | |

Directives 1 to N, Users 1 to M, Resources 1 to R

FIGURE 8

Listing

| Time | policyName | repo | status | username |
|---|---|---|---|---|
| Jan 17, 2021 @ 22:53:23.181 | GeoLocationTest | perf | AUTHORIZED | james@yopmail.com |
| Jan 17, 2021 @ 22:53:17.600 | GeoLocationTest | testrepoprod | AUTHORIZED | james@yopmail.com |
| Jan 14, 2021 @ 07:30:03.294 | GeoLocationTest | testrepoprod | AUTHORIZED | james@yopmail.com |
| Jan 14, 2021 @ 07:26:39.135 | GeoLocationTest | testrepoprod | NOT_AUTHORIZED | james@yopmail.com |
| Jan 14, 2021 @ 07:12:54.070 | GeoLocationTest | testrepoprod | NOT_AUTHORIZED | james@yopmail.com |
| Jan 14, 2021 @ 07:11:49.170 | GeoLocationTest | testrepoprod | NOT_AUTHORIZED | james@yopmail.com |

FIGURE 10

SYSTEM AND METHOD FOR DIRECTIVES BASED MECHANISM TO ORCHESTRATE SECURE COMMUNICATIONS IN MULTI-CLOUD DISTRIBUTED SYSTEMS

FIELD

The disclosure relates to access control in computer network systems and in particular to access control in multi-cloud distributed systems to orchestrate secure communications.

BACKGROUND

Traditional systems today are complicated with a rapid sprawl of infrastructure, a number of security tools deployed and the large number of users getting provisioned and/or de-provisioned for access permissions to one or more parts or resources of these traditional systems. The traditional method of controlling system access through authenticating users and their entitlement to access resources is ineffective and has technological problems. The technical problems include limiting the ability to enforce the central security directives granularly at every level of the hierarchy and that the systems/methods do not take into consideration the multiple roles played by the users at the various stages of system and application workflows.

Current identity management systems have evolved Role based Access control in which the attribute based (based on the role of the user) access focuses on ensuring that the users with the right access rights can access and manage system resources. However, due to the changing nature of roles played by the users and the privilege trawl (which is the rapid and uncontrolled proliferation of privileges), it is challenging to keep track of the access privileges of each user when the user has multiple roles. This leads to hidden assets and privileges which are subject to anomalous behaviors which is challenging to keep track of in real time which weaken the technical strength of the current identity management systems.

FIG. 1 illustrates some of the challenges of a traditional identity management approach. In the example in FIG. 1, the organization may include an ecosystem, supply side partners, in-house people, customers, demand side partners and third parties who may each have one or more roles and one or more different access privileges that need to be controlled and managed. The organization will have organizational security policies and access privileges that need to be managed. Traditional identity management approaches mean that the organizational security policies and access privileges are not consistently enforced for several reasons shown in FIG. 1. One reason for failure is asset pilferage in which IT decision makes in the organization discover hidden endpoints (resources, new devices with access privileges, etc.) that were previously unknown to the IT decision maker. These unfortunate discoveries occur on a weekly basis. Another technical problem is permissions pilferage the permissions of users are not in compliance with the organizational policies. Furthermore, least privilege access does not address all of the needs of multiple user roles. Additional failing of the known system are shown in FIG. 1.

Thus, it is desirable to provide an identity management system and method that overcomes the above technical issues with traditional identity management systems and it is to this end that the disclosure is directed.

BRIEF DESCRIPTION OF THE DRAWINGS

FIG. 8 illustrates an example of a directive access dictionary;

FIGS. 9 and 10 illustrate examples of the user interface of the directives access system;

DETAILED DESCRIPTION OF ONE OR MORE EMBODIMENTS

The disclosure is particularly applicable to an identity management system using a novel lineage traceability enforcement engine to manage secure communications in multi-cloud distributed system and it is in this context that the disclosure will be described. It will be appreciated, however, that the system and method has greater utility since it can be used for any system in which it is desirable to provide identity management while overcoming the technical problems and limitations of the known systems as described above.

In the illustrative embodiment, the identity management system and method may provide a directive based access control mechanism using a novel lineage traceability enforcement engine to orchestrate effective secure access control and communications in multi-cloud distributed systems. The directive based access mechanism effectively defines, manages and controls security directive mandates. One of the ways to implement the Directive based access system is utilizing Lineage Traceability Enforcement Engine. However, the disclosed directive based access control system may also be implemented using other known or yet to be developed systems such as Blockchain based Hyperledger based system and the like.

Figure 1:
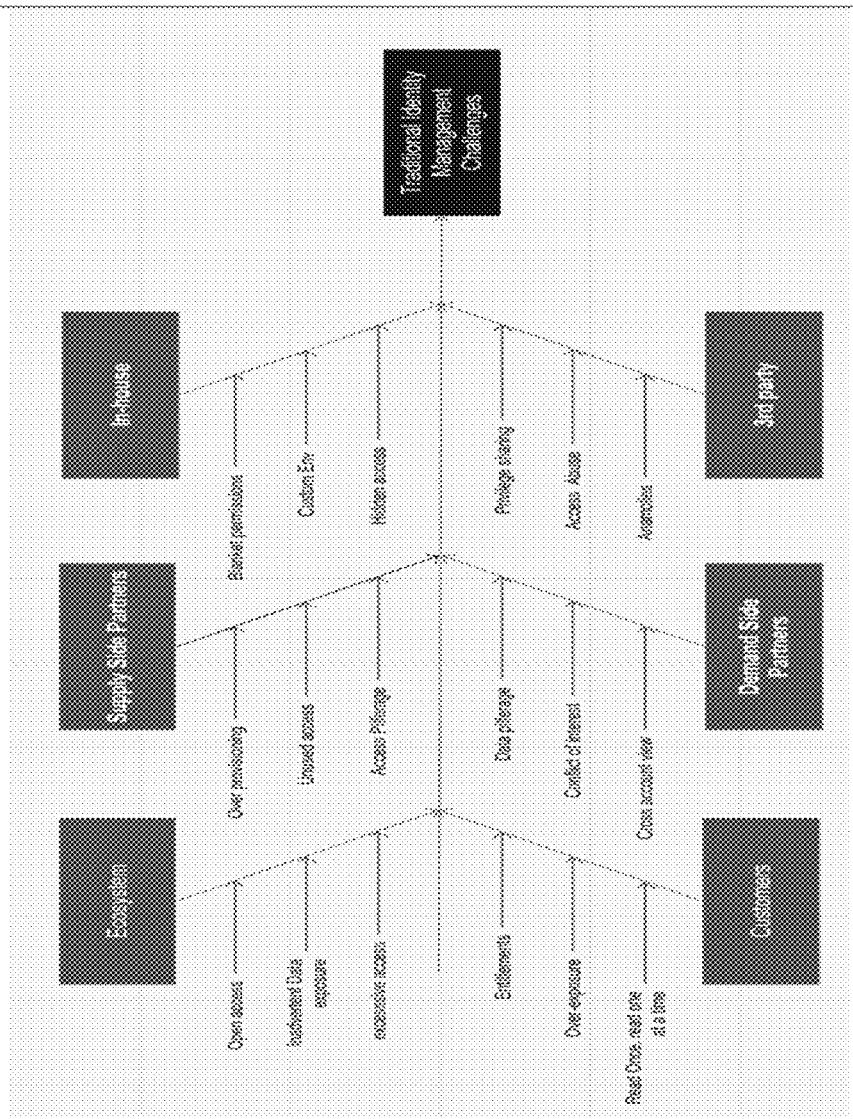
FIG. 1 illustrates some of the challenges of a traditional identity management approach.
Figure 2:
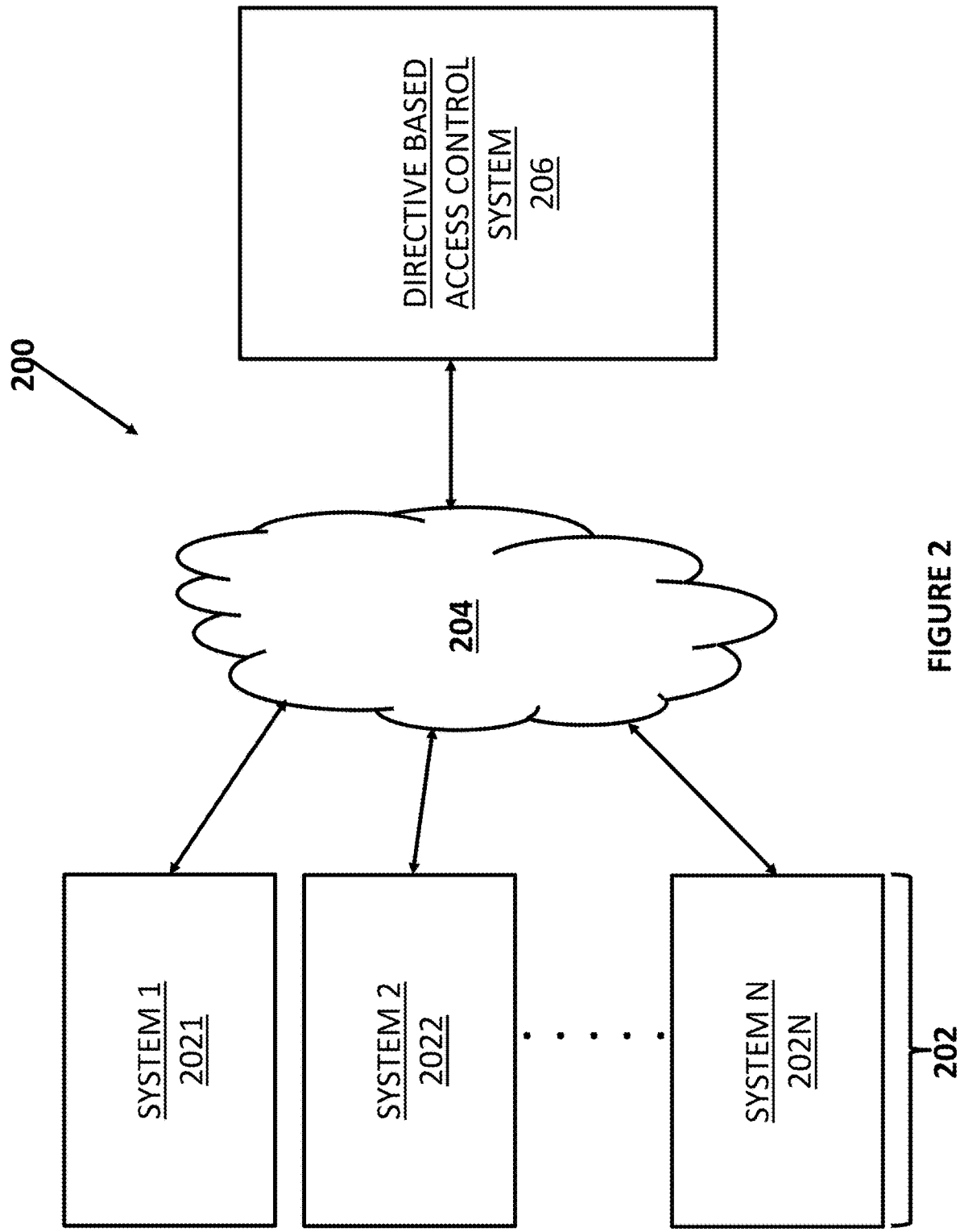
FIG. 2 illustrates an implementation architecture for a directive based access control system.

FIG. 2 illustrates an implementation architecture for a directive based access control system 200 for controlling access control and identity management within a network or system that has a plurality of sub-systems/resources/devices/elements that each have access control requirements that are managed by the entity that controls/owns the overall network or system. Thus, as shown in FIG. 1, the system may have one or more subsystems 202, such as system 1 2021, system 2 2022, . . . , system N 202N, whose access permissions are controlled. Each system 202 may be a system or resource or device that are connected together in the system. For example, each system may be a server computer, an application server, a database server, a database, a firewall device, a personal computer, a laptop computer, a mobile computing device, such as a iPhone device and Android operating system device and the like that all have at least a processor and memory. Each system 202 may further have a plurality of lines of computer code/instructions that are executed by the processor of each system 202 that configure the system 202 to enforce the access control policies of the entity.

Each system 202 may connect to and communicate over a communication path 204 (that may be wired or wireless, a cellular network, a digital computer network and the like) with a directive based access control system 206 that may be geographical distance from the systems 202 or located in the same data center or cloud based resource. The directive based access control system 206 may store a plurality of access control policies for each of the systems 202 and implement those policies to manage the access control to the systems 202 and identity management of the users of the system. The directive based access control system 206 may be implemented as one or more computer systems with at least one processor that executes a plurality of lines of computer code/instructions so that the system 206 and its processor are configured to perform the various access control/identity management processes discussed below in more detail.

Figure 3:
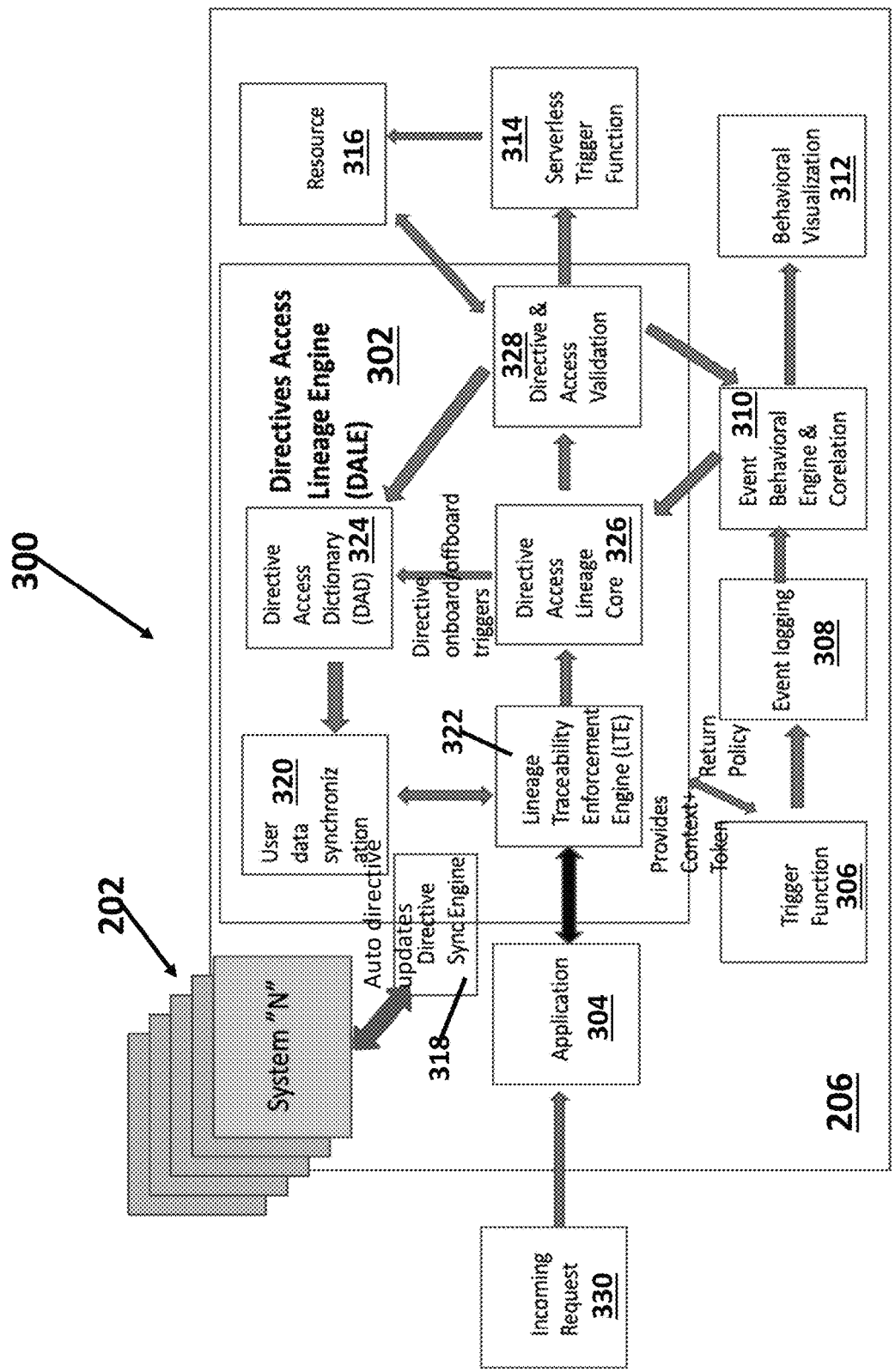
FIG. 3 illustrates an implementation of the directive based access control system using a directive access lineage engine.

FIG. 3 illustrates an implementation of the directive based access control system 300 using a directive access lineage engine (DALE) 302 as part of the directive based access control system 206 that controls the access to the systems 202. More details of the directive based access control system 206 are shown in FIG. 3 including an application 304, a trigger function 306, an event logger 308, an event behavioral engine and correlation engine 310, a behavioral visualization engine 312, a serverless trigger function 314 and a resource 316. The application 304 is each application that interacts with the system 300 to execute transactions with the system infrastructure based on the directive access using DALE 302. The trigger function 306 represents an upstream trigger function to execute directives based on the determination of entitlement by a directive access dictionary (DAD) 324. The event logger 308 is an event logging infrastructure/system which serves as a repository of all the incoming and outgoing events in the system 300. The event behavioral engine and correlation engine 310 that monitors the behavior of the events logged and correlate them for determination whether the events align with directives defined in the DAD 324. The behavioral visualization engine 312 generates a behavioral visualization of all the events while the serverless trigger function 314 ensures enforcement of directives over resources. Each resource 316 is a resource on which the security directives are applied as described below in more detail.

The directive access lineage engine (DALE) 302 has a directive sync engine 318 that synchronizes the various access directives/permissions developed by DALE (including DAD 324) with each of the systems 202 being managed using DALE. Each system 202 may receive the same directives or different directives or some of the same directives and some different directives depending on the system 202. In a scenario involving AWS, Azure and Google Cloud, the goal for the DALE engine is to ensure that the defined set of directives are a) consistently applied, monitored and enforced across all the 3 cloud assets or b) the setoff directives are customized for each of the cloud systems individually or c) both a and b applied to varying degrees. DALE 302 may also have a user data synchronization engine 320 that exchanges data with a lineage traceability enforcement engine (LTE) 322 and synchronizes the user data interacting with the system 300 and LTE 322 maps the behavior of the directives being enforced on all the users and resources in each of the systems 202A-N. The behavior mapping is the process of tracking and mapping the behavior of all the system components (users, resources, activities, etc.) against the defined directives in the DAD 324 and identifying the alignments as well as the gaps with respect to the directives. For example, a directive XYZ may specify that a person subject to the directive can access system resources only twice a day, not more than single access within each hour and no download of the file (collectively "access rules" that include access rights and access limitations and constraints). An external user of the system may be subject to directive XYZ. The behavior mapping engine tracks the user behavior against this specific directive and identifies compliant and non-compliant behavior of the user relative to XYZ directive and other directives that govern the access of the external user.

DALE 302 also has a directive access dictionary (DAD) 324 that is connected to the user data synchronization engine 320 and is a repository for all the directives of the organization (examples of which are discussed below in more detail.) DALE 302 may also have a directive access lineage core 326 that is the core processing engine to uphold the directives defined in DAD 324 at all times using a directive and access validator 328 that is the decision engine to allow/deny incoming events requests for access to resources and users in systems N based on the directives of the organization.

The Directives and Access Lineage Engine (DALE) 302 is a comprehensive Lineage engine that defines one or more directives of an organization/entity who owns/manages the overall system 200. DALE 302 monitors and enforces those directives across the systems 202 hierarchy within and outside the organization irrespective of the users, assets and infrastructure involved. For example, the directives may be used: 1) to centrally manage the ownership of data in a hospital, including who has access to what, when and how (circumstances/scenarios) and constantly ensure alignment with the directive(s); 2) by a procurement organization ensuring that the organizational directive related to who is entitled to what, workflow compliance, prevention of conflict of interest, repudiation, etc are followed; and 3) as organizations directives for infrastructure and data access to third party vendors which is enforced at all times. DALE 302 is implemented using a Directive Lineage based Access Control (DLBAC) mechanism where all the entities involved in a system—infrastructure, users, resources, permissions are driven by directives lineage. DALE 302 also provides auto Directive orchestration—orchestrates permanent, transient, active and passive policies through the DLBAC driven Security Directives platform; dynamically onboard and offboard users, resources and behaviors in order to accomplish specific outcomes as mandated by the DALE engine; and enforce Directive mandates across users and resources irrespective of their privileges and past entitlements.

DALE also orchestrates auto-directive updates to DAD 324 based on genuine transient behavior emanating from the Systems N. For example, the owner of a house shares the security codes of his/her house with a friend to be able to enter the house once a week. Over a period of few days, the friend realizes the need to visit the house more than once a week to address genuine tasks such as fixing the gas leak in the house or a water leak in the bathroom or a rodent infestation in the house while the owners are away. Based on the friends genuine needs the system makes auto-directive updates to enable the friend to visit the house more than once a week with the owners approval. The auto directive updates are defined, processed, updated based on user and resource requests along with their historical behavior. In one embodiment, the auto-update system is executed using machine learning and Artificial Intelligence algorithm of the event behaviors (discussed above) before updating DAD 324.

Directives and Access lineage is a lifecycle that traverses the organizations directives and access origins and where it moves over time and place. This term can also describe what happens to the Directive directives and access as it goes through diverse processes including behavioral changes of systems, resources, users and Directive directives. Lineage based access can help with efforts to analyze how accesses are used and to track the behaviors of each of them in alignment to the centrally managed Directive directives which are executed across the Directive directives lifecycle.

In operation, each income request 330 is processed using user identity and data synchronization service in order to authenticate users using JWT token from user pools. To validate the token and give them necessary permissions, the system implements a custom authoriser in the API Gateway that is basically a serverless function. From the custom authorizer, the DALE system 302 implements custom logic that can validate the application API access permissions. Based on each incoming access request 330 to data, provisioning, or instantiating applications is synchronized and validated by the User data synchronization block 320 and processed on to the Directive Access Lineage Core 326 for lookup from the Directive Access Dictionary (DAD) 324 to determine alignment of the access request to the directives and to generate an approve or deny result in response to the request 330 which is then passed on to the serverless trigger function 314 to then process the event request action for downstream activities (that may include sending the response onto the resource 316 about which the access request was made). Simultaneously, the trigger function 306 continuously logs 308 and monitors the contextual behavior of the event requests to correlate the behaviors (using event behavioral engine 310) to process for anomalies and exception request approvals and update the DAD 324 accordingly. This process is repeated for all the N systems in consideration and each access request.

Figure 4:
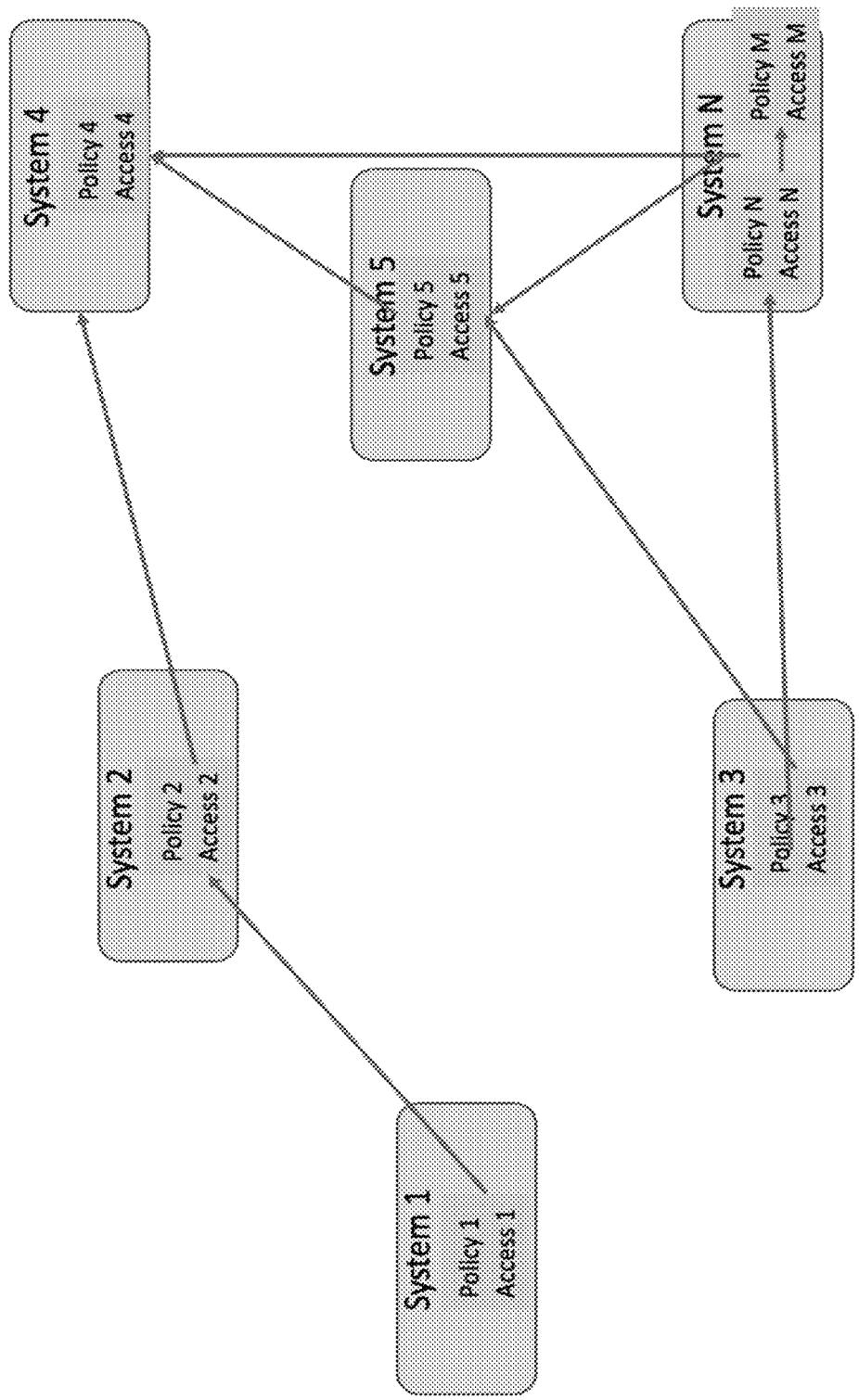
FIG. 4 illustrates an example of a system with subsystems and the directives and access for each subsystem and the overall system.

For example, an incoming request by the system resource or users first gets authenticated in the system to identify the affiliation (API request or Internal user/resource or external user/resource or customers, etc. The incoming request goes through validation (based on their respective lineage (path/ position in the hierarchy) with lineage traceability engine 322, DALE core processing 326 and Validation module against the DAD module 324 and then gets orchestrated through a return function which carries the approval or denial flag The directives access based lineage used by DALE 302 is important. The importance of the directives access based lineage which is that it allows the system to track the access lineage in alignment with Directive directives through an organization, which in turn is helpful for tracking anomalous behaviors, errors, quality issues and uncovering any potential impact on the dilution in the enforcement of the directives. FIG. 4 illustrates an example of a system with subsystems and the directives and access for each subsystem and the overall system. If there is an anomaly in one of the directives and access combination (P+A) of a particular system (such as system 1 that has Directives 1 and access 1), or a particular directive or access is changed, the directives access based lineage allows a user/administrator to easily see what other systems are impacted by the anomaly. For example, if (P+A) 3 in Application 3 is changed, this will impact systems 5,4, & N as shown in FIG. 4. While this is an extremely simplified use case, the directives access based lineage provides accurate (P+A) lineage that permits the system to determine confidently whether or not a change is going to have a large impact on the resources access upstream or downstream of the affected system. For example, a HIPAA policy which controls the handling of Patient data is orchestrated hierarchically. As a result, a primary policy of the system directs the set of policies for a healthcare provider hospital to comply on patient data management which is then spawned to the downstream hospital and further to users (staff, doctors, nurses, patients, etc) of the hospital. Then, any changes in the primary system 1 will affect the downstream healthcare providers in system 2 or 3 automatically due to the directive lineage without the subsidiary directives or the subsidiary systems needing to be reconfigured.

Figure 5A:
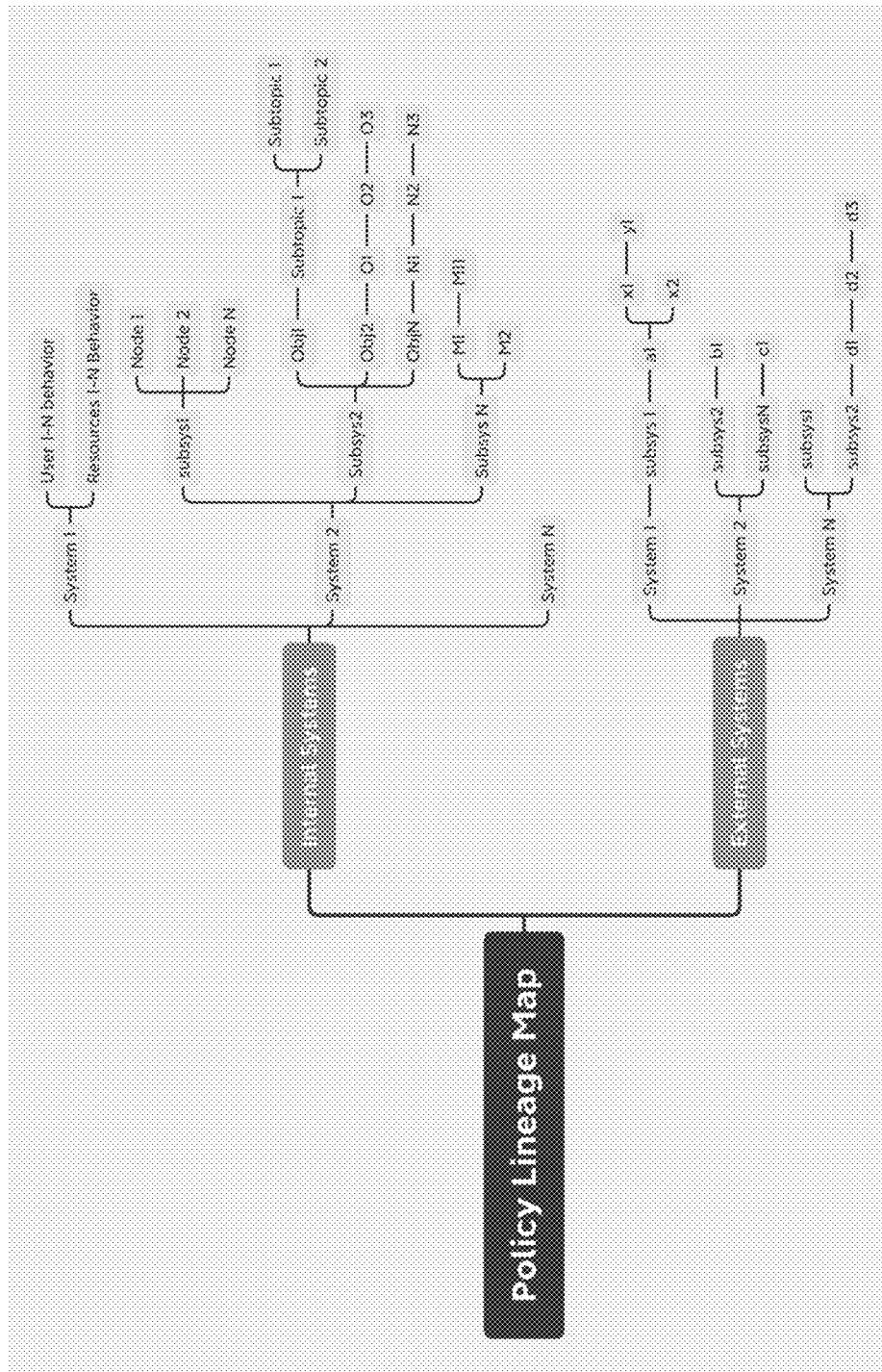
FIG. 5A illustrates an example of a directive lineage tracing map.

FIG. 5A illustrates an example of a directive lineage tracing map 500 that is generated by DALE 302 for an example of a system whose sub-systems are being controlled by the DALE 302. As shown in FIG. 5, the map 500, in this example, has an internal system node and an external system node. Within each of these nodes are subnodes for systems of the overall system that are part of the higher level node so that the internal systems node may have a subnode for each system or sub-system that is an internal system. As shown, there may be further subnodes for user behavior or resource behavior for a particular system, subnodes or subnodes of the system, objective policies (possible with subtopics), etc, to form the map/tree of the access control lineage for the system. Each of O1, O2, N1, N2, M2, etc are the nodes or endpoints in each of the systems wherein each node represents different entities and may carry their own specific attributes. The bottom of a branch in the map/tree may be known as an lineage endpoint that can be updated, added or removed by the lineage traceability and enforcement engine 322.

Figure 5B:
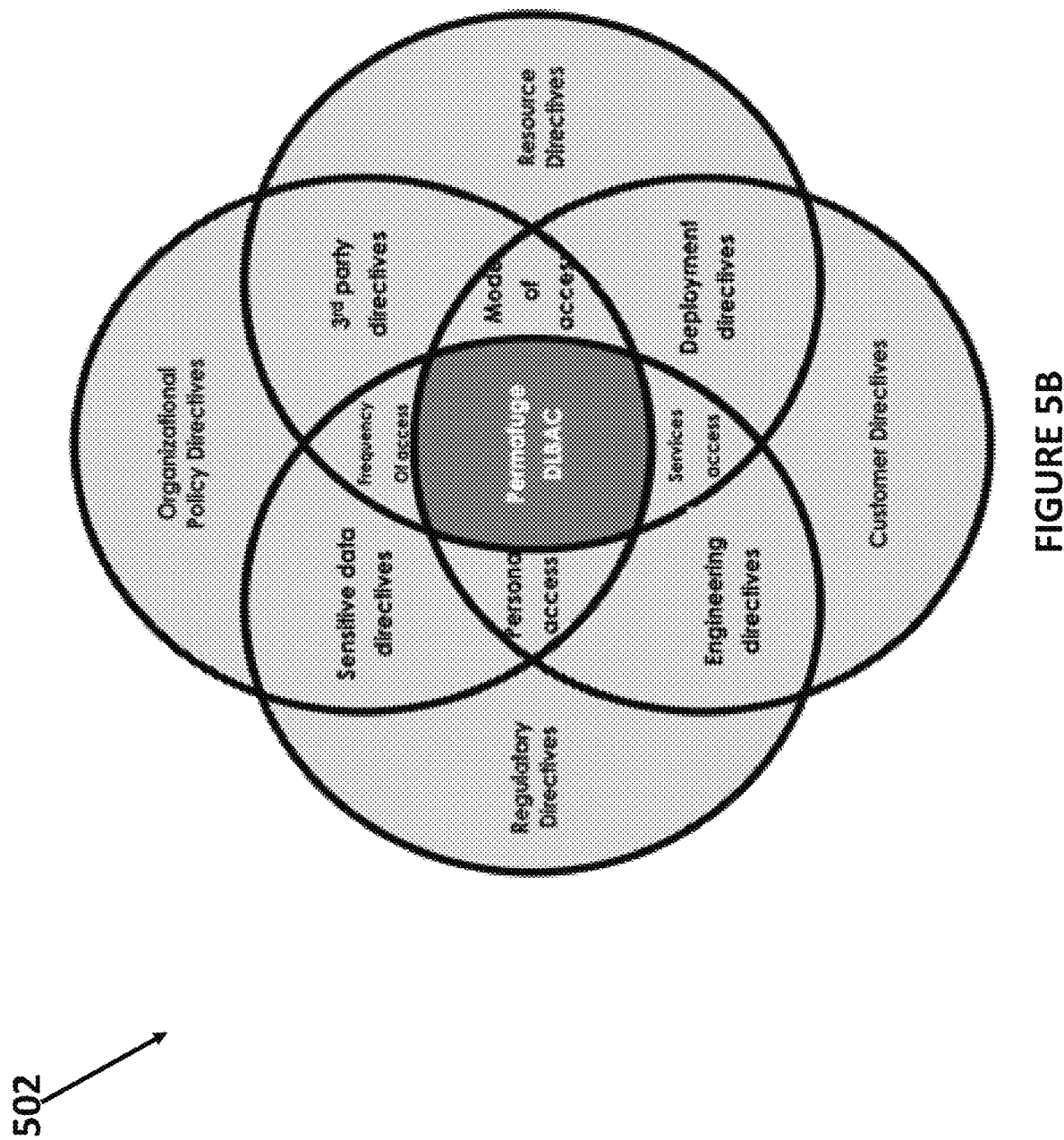
FIG. 5B illustrates an example of a set of directives for an entity or enterprise.

FIG. 5B illustrates an example of a set of directives 502 for an entity or enterprise. The set of directives may be agnostic to the infrastructure, users and applications and supports customer's scale in alignment with their security mandates. The set of directives support distributed assets and workflows and establishes the directive lineage and controls. The set of directives also supports multi-directive clusters. As shown in FIG. 5B, the set of directives may include one or more overlapping directives that result in the directive lineage based access control (shown in Permafuge DLBAC in FIG. 5B.) The set of directives may include broad organizational directives (such as organizations security policies for employees of a hospital), regulatory directives (such as organizations mandates that comply with HIPAA directives), customer directives (such as end customer directives on personal information sharing), and resource directives (such as technology directives on using Amazon Web Services tools). The set of directives may further include directives that are based on one or more of the broad directives and may include sensitive data directives (such as PII data/Electronic Health Records), third party directives (such as mandates of third party vendors like payroll systems provider ADP), frequency of access directives (such as a number of times that a hospital nurse can access patient records within a day/month/year/etc.), personal access directives (such as an ability to download data in the local storage), mode of access directives (such as access through organization provided devices/bring your own devices (BYODs) or personal devices, etc.), service access directives (such as how do the different microservices access the same repository of data and prioritization of access), deployment directives (such as mode of usage of data in applications) and engineering directives (such as ensuring security directives for application development and maintenance).

Figure 6:
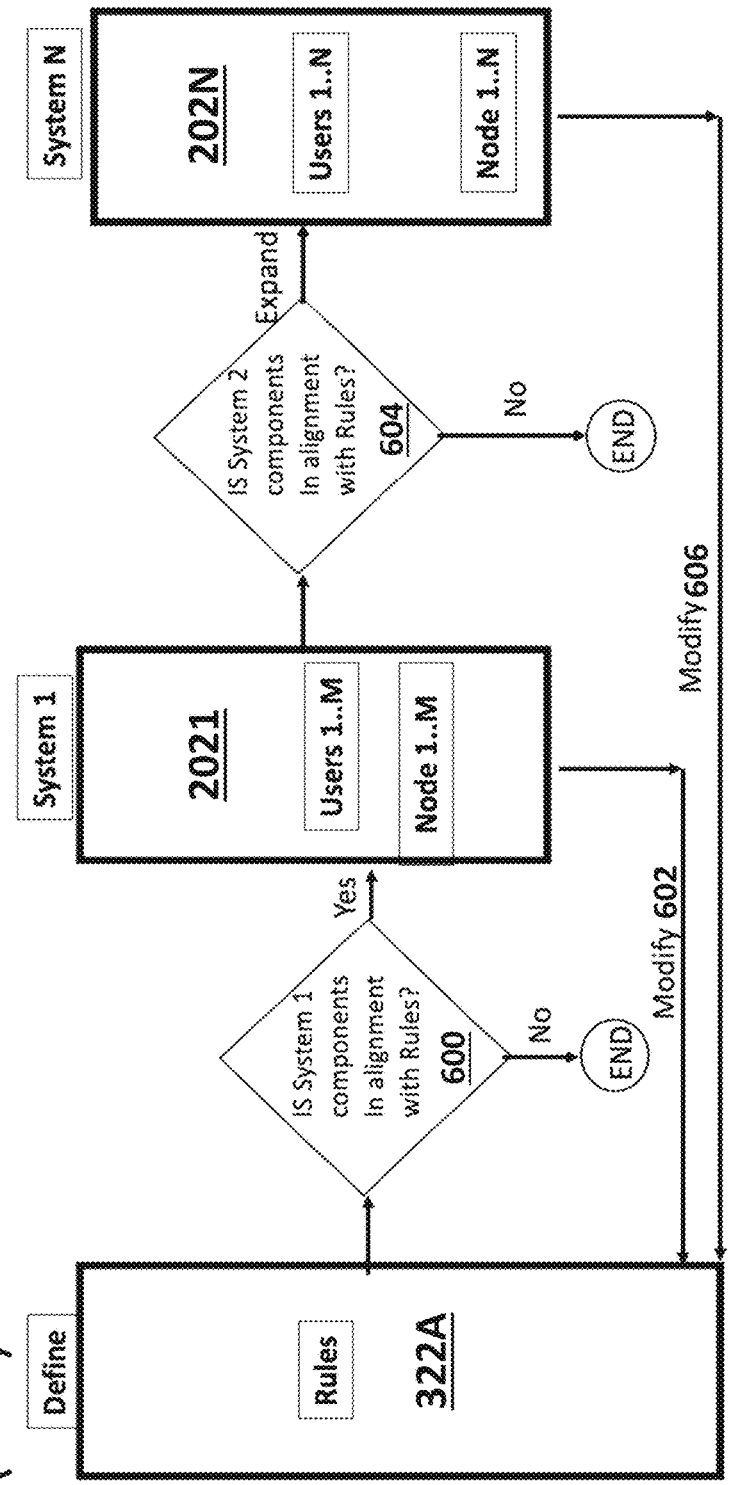
FIG. 6 illustrates more details of the lineage traceability and enforcement engine of the identity management system.

FIG. 6 illustrates more details of the lineage traceability and enforcement engine 322 of the identity management system. The lineage traceability and enforcement engine 322 expands or terminates the lineage endpoints based on the adherence to centralized security directives wherein the DALE engine 302 creates a contour of systems and components creating a traceability map of security directives across systems resulting in continuous expansion, termination or updating of the lineage maps based on changes or updates to the directives and the associated alignment of the system components to those directives. As shown in FIG. 6, each system (2021, 202N in this example) has a set of users (users 1 . . . M and 1 . . . N in this example) and a set of nodes (nodes 1 . . . M and 1 . . . N in this example) that may be affected by the access rules.

As shown in a simple example in FIG. 5 for two systems 2021, 202N whose access is being controlled by the system, the lineage traceability and enforcement engine 322 have many a set of access permissions/directive rules 322A. An example of these set of rules are shown in FIG. 5B and described above. In the example in FIG. 6, the two systems 2021 and 202N access permission status is unknown and then the LET 322 performs a process of lineage traceability and enforcement. Thus, using these rules, the LTE 322 may determine if system 1 components are in alignment with the rules (600) For example, if a user/users makes a request for a particular system/resource access or transaction and that request is in alignment with the directive defined, then the user may be granted access since the request is in alignment with the resource access directive. If the system components are not in alignment, then the access rights are terminated for the system components. If the components are in alignment and need a change in the directive for genuine system requirements, then a modify command 602 may be sent back to the set of rules 322A.

For example, the defined directives in the DAD module 324 enable changes in the directives to accommodate genuine new or different system requirements based on changing scenarios. For example, an approver in a procurement/sourcing function requires access to systems A, B and C to execute his activities of approving business contracts. During the course of execution of his/her activity, the user realizes the need for additional resources (documents) in system D which he/she doesn't have. Based on the genuine business requirements, the approver makes an exception request to update the specific directive in DAD 324 and granted access to system D based on the new scenario. As another example, a homeowner grants access to a friend to visit the house while the owner is away once a week, however due to new situation in the home due to water leakage and other issues in the house, the friend needs to visit the house more than the requested once a week. Based on the genuine activity of the friend and the need, the friend's access to visit the house is increased by the DALE system.

If the system 1 is in alignment, then the LET 322 checks to determine of system N components are in alignment with the rules (604). If the system components are not in alignment, then the access rights are terminated for the system components. If the components are in alignment, then a modify command 606 may be sent back to the set of rules 322A. In this manner, the LET 322 performs lineage tracing and enforcement.

Figure 7:
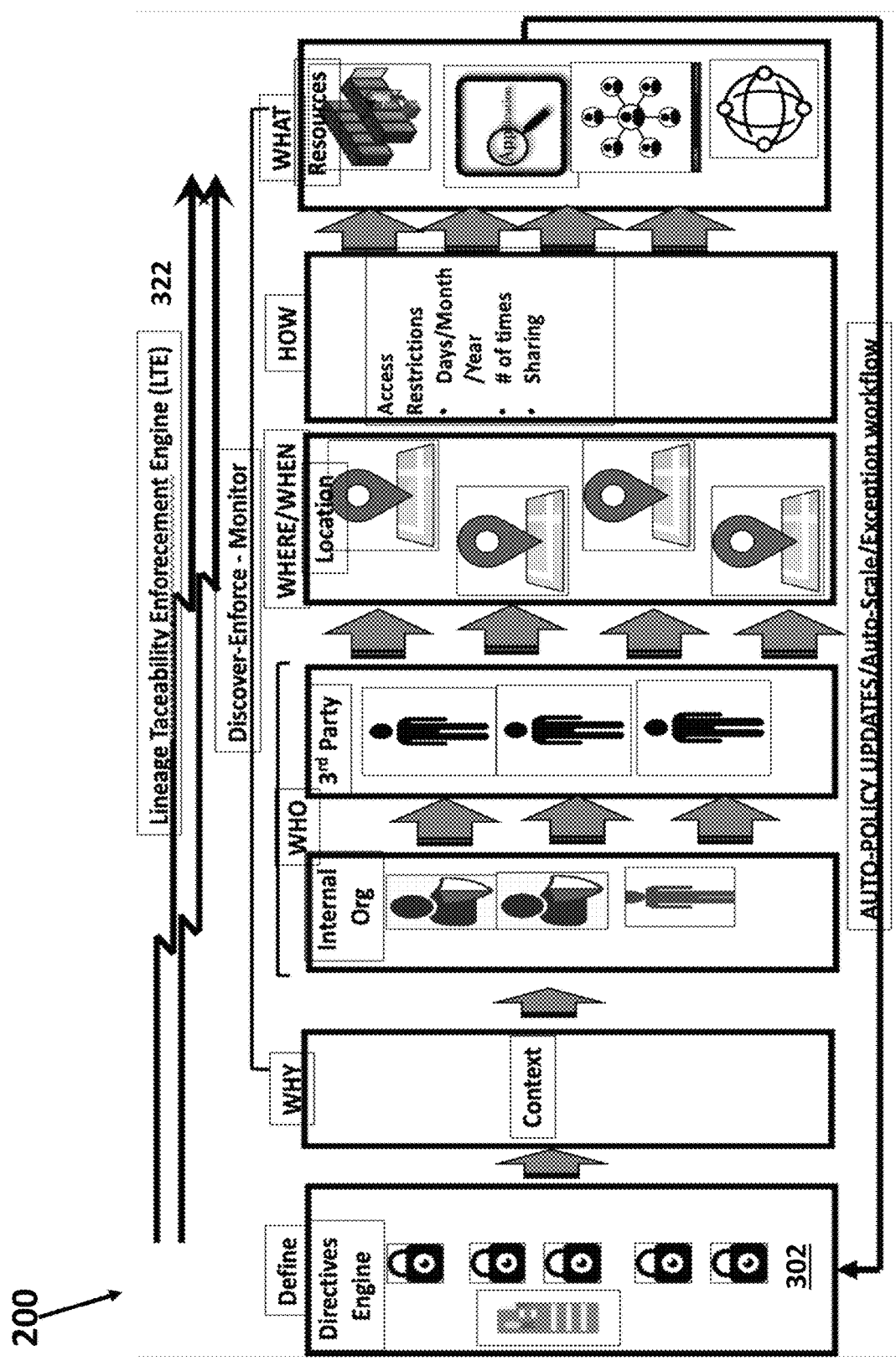
FIG. 7 illustrates a high level functional block diagram of the system; \

FIG. 7 illustrates a high level functional block diagram of the system 200 including the directive access lineage engine (DALE) 302 that defines the directive and access rules for the internal organization and third parties access to the system 200 and its resources. As shown in FIG. 7, the LET 322 may trade the lineage as discussed above. The system 200 may also have auto-directives updates and workflow that is the same as the modification process described above. As an example, the system whose access is being protected may be a residence in which the owner has defined a directive in their house system to enable their friend to get access to their house once a month to take care of certain errands. The friend discovers that he/she needs to visit the house 3-5 times a month to take care of certain things in the house, like watering the orchids, mowing the lawn, etc. The auto-directive update feature shown in the loopback system will effectively address the need for additional access based on the number of visits that the friend has to make to take care of the tasks that was originally not accounted for.

FIG. 8 illustrates an example of a directive access dictionary 324. The directive access dictionary 324 has various columns with each characteristic for each security directive including a name, a context, resources (file or repository) subject to the directive, expiration of the directive, a sharing parameter, a maximum access attempts, a number of access attempts in a period of time, read/write/delete/create/terminate rights, write access, delete access, geo location allowed, download access and time of access. It is understood that each directive may only have one or more (but can be all) of these characteristics specified. For example, as shown in FIG. 8, a "1 to N" security directive has a context (situational privilege of user 1 to M enabling alignment with Directive 1) to resources 1 to R.

For example, a maintenance person for an ATM needs access to the specific ATM xyz machine to roll out an upgrade. In order to achieve this, the maintenance person's directive is defined as having access to ATM machine xyz on Saturday Oct. 23 2021 between 11 am pacific time till 12 noon pacific time, access only in person (no remote access), cannot share access with others, only 1 access attempt, can only read files and folders and can execute access on the new build/upgrade only. As another example, doctors can read any data of patients in the same specialty as themselves and update patient profiles, journals and medication records of patients that they treat, but nurses can only access medical records of their patients and patients whose current treating physician is the same physician who the nurse is currently assigned to assist and only if the nurse is currently badged into the same physical building as the location of the patient. As shown in the examples above, the one or more directives are unique crafted for each user case and the resources involved for the use case.

The Directive Access Dictionary 324 is a dynamic rule engine with behavioral based auto-directive updates establishing a relationship and rules of engagement based on Lineage between directives and incoming requests. The intent of DAD 324 is to establish visibility of enforcement of directives across the lineage of the system and enforce the rules of engagement. The auto update mechanism ensures on-going review of the directives based on the genuine needs of the workflows and activities to go beyond the constraints set by the directives for the access of resources and update them accordingly to better suit the systems needs. The DAD 324 may also provide the context/conditions under which DALE engine 302 onboards and offboards policies. The onboard/offboard process is the mechanism which is dependent on the genuine or malicious behaviors of the systems and its entities. Offboarding of systems' entities to take place where in anomalous behavior (anomalous intent to perpetrate abuse including excessive access, advertent or inadvertent attempts to change configurations of resources or users, data pilferage attempts, etc.) Onboarding of systems' entities to take place when there are genuine requirements for activities involving system entities need add/update of policies.

Figure 9:
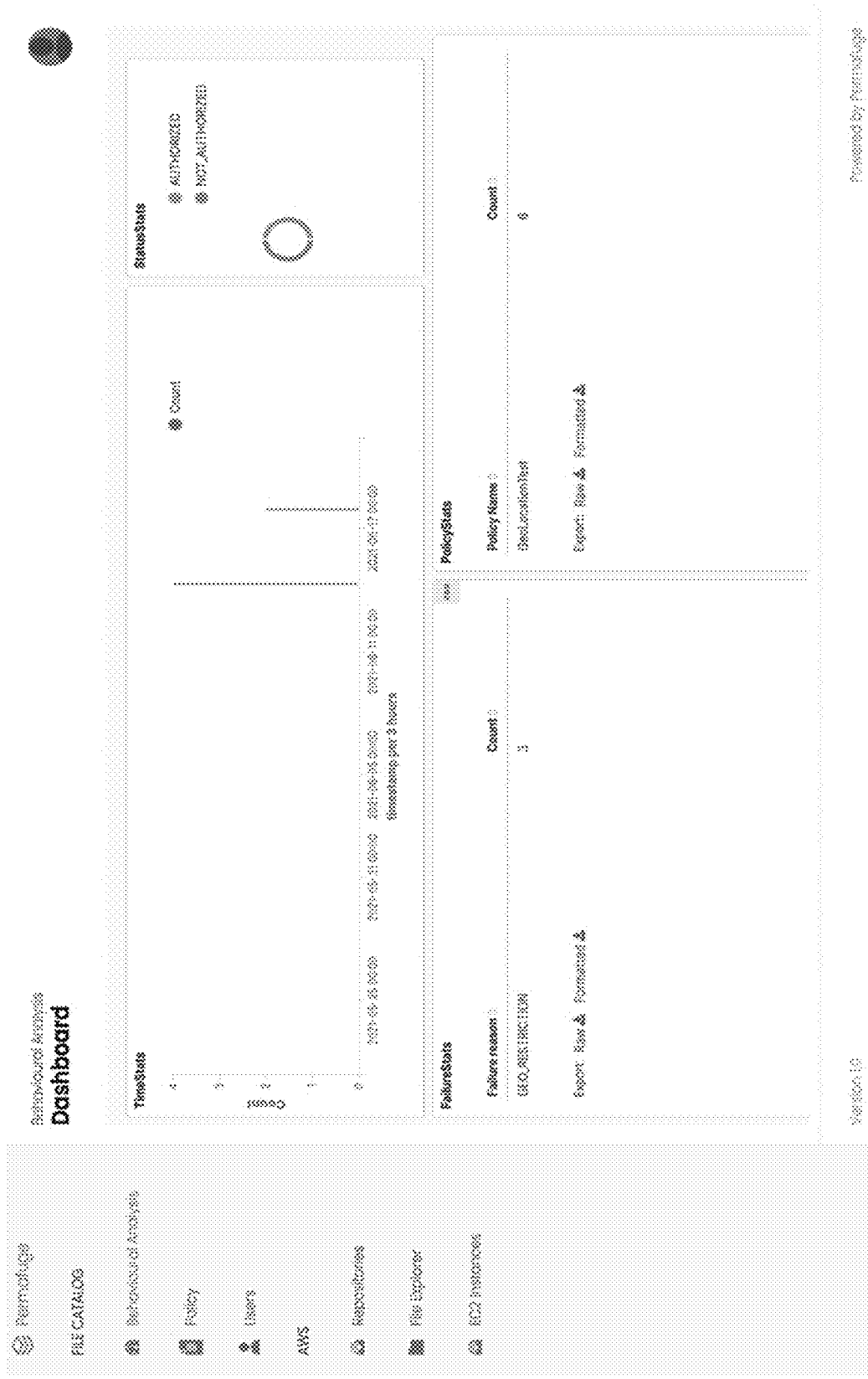

FIGS. 9 and 10 illustrate examples of the user interface of the directives access system in which FIG. 9 shows the dashboard of the system and FIG. 10 shows a listing of the access being granted or not based on the directives. The system and directive and access lineage engine (DALE) 302 is a system for effectively tracking centralized security directives, resources and users in distributed systems to provide an inside-out method of forcing alignment of system transaction with dynamic security directives irrespective of prior privileges and entitlements associated with users over resources, accounts and their roles across different transaction systems.

DALE 302 implements a heart-beat to onboard/offboard/update directives based on changing scenarios necessitating changes in the DAD 324. The system co-relate the entitlements of the incoming requests against the DALE 302 and performs triage based on the defined mandates. The wrapper function shown above triages incoming requests and authenticates the entitlement of participating in a particular Directive. The trigger function module facilitates the transaction enablement based on the necessary conditions met for the facilitation of the incoming event. Unlike known and conventional access control policies which establish entitlement based on user and role privileges, DALE 302 orchestrates the participation of users and resources based on their entitlement to participate in execution of a Directive mandate. Thus, instead of the need for defining roles for every user on what/where/how to access, DALE ensures that all the required entities in enforcing Directive mandates across the entire systems' boundary.

Using the above directive access and lineage system and method may be used to control access in a number of different organizations including heathcare, a telco and in sourcing/procurement as will now be described in more detail.

Healthcare Use Case

Figure 11:
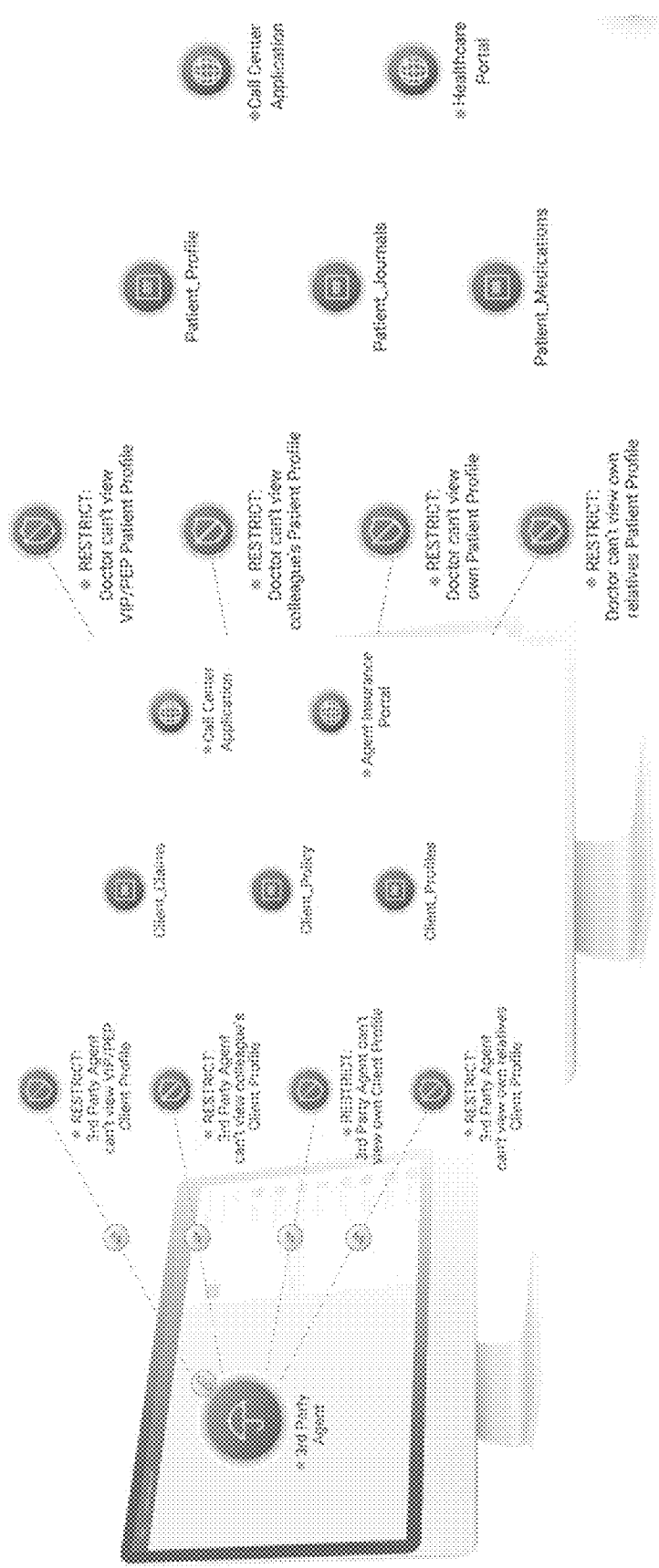
FIGS. 11 and 12 illustrates a healthcare use case with directives for the different entities.
Figure 12:
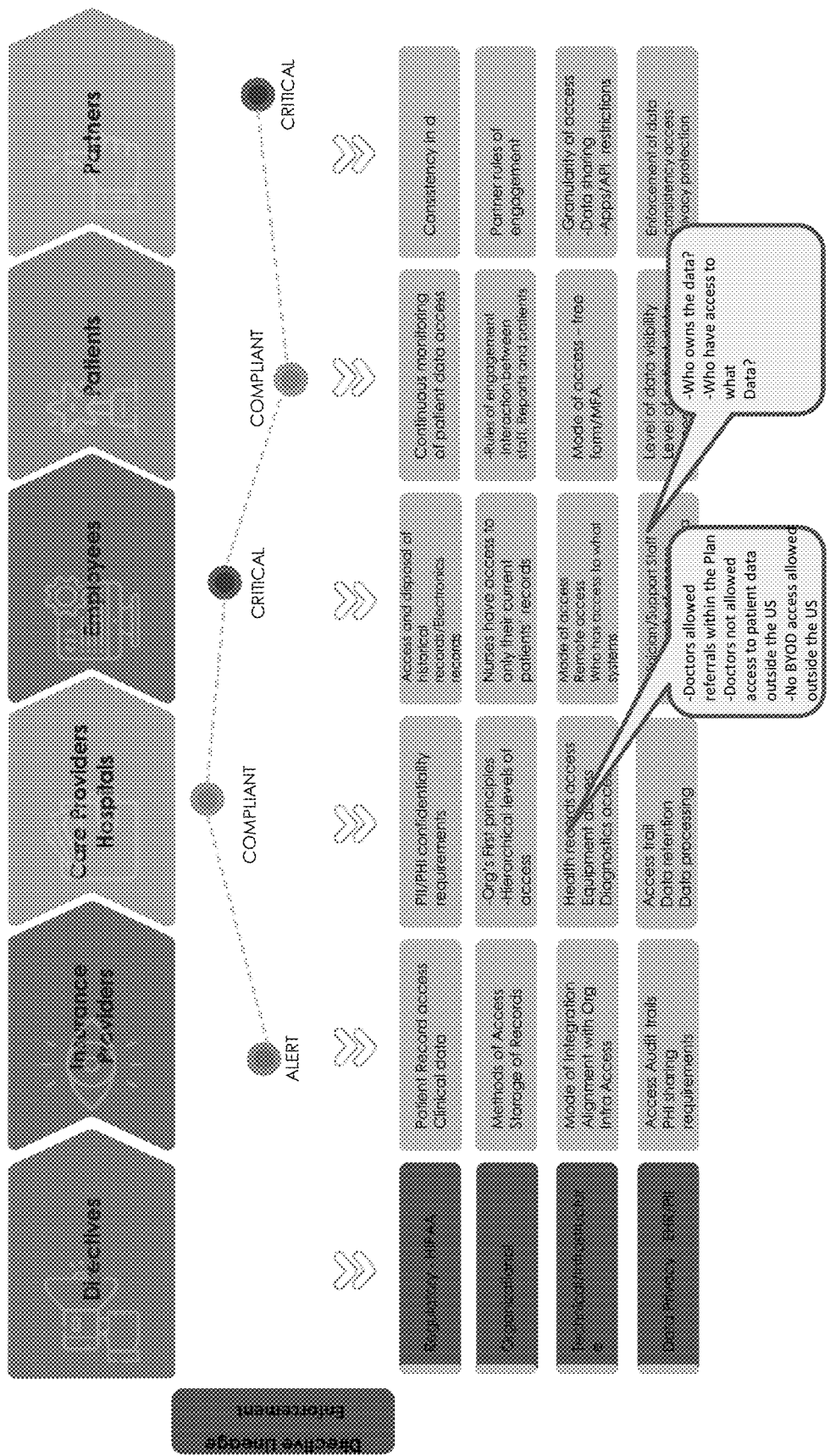
Figure 13:
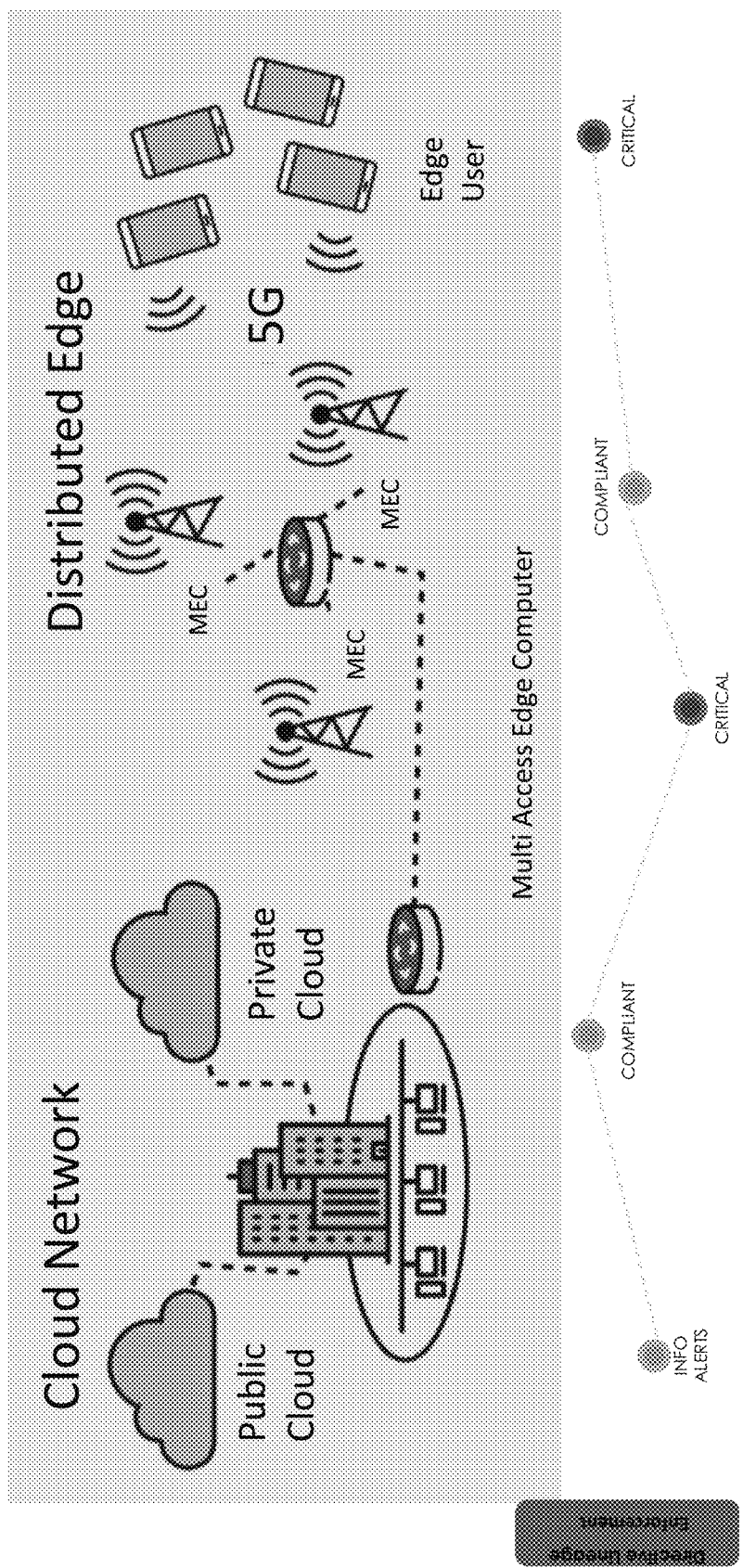
FIG. 13 illustrates a telco security policy enforcement use case.
Figure 14:
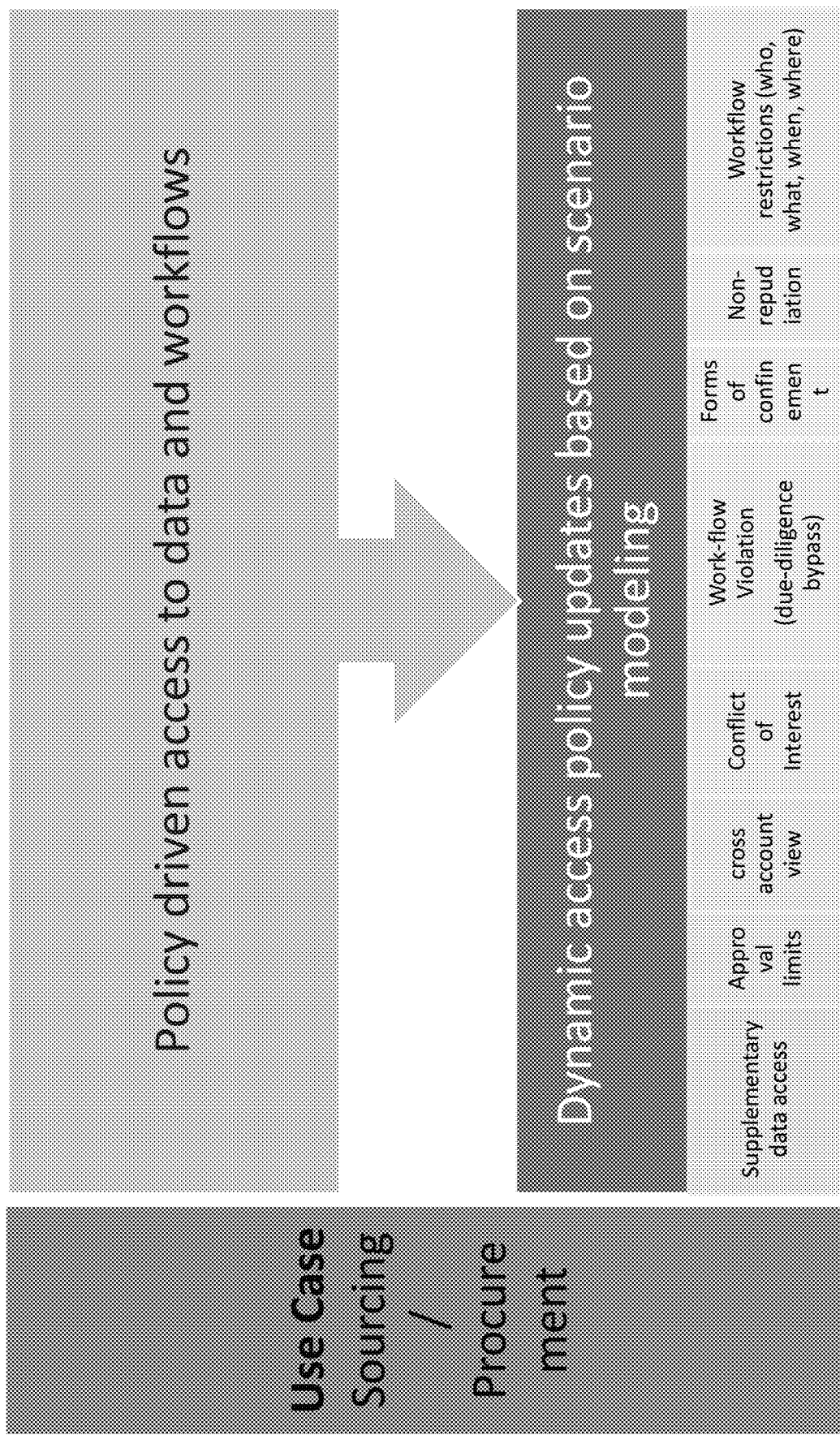
FIG. 14 illustrates a sourcing/procurement use case.

FIGS. 11 and 12 illustrates a healthcare use case with directives for the different entities. As shown in FIG. 11, the directive access control system may be used to control access to patient data and thus this use case has a set of directives to control access to the patient data. FIG. 12 shows the different directives and entities (insurance provider, care providers/hospitals, employees, patients and partners) whose access is controlled by the directive access control system. Note that each use case may have its own set of directives that are geared to the particular use case. Thus, for this healthcare use case, the set of directives may include a regulatory/HIPAA directive, an organizational directive, a technical/infrastructure directive and a data privacy directive as shown in FIG. 12. For each different entity, each directive may have a set of directives for that entity. Thus, for example doctors can read any data of patients in the same specialty as themselves and update patient profiles, journals and medication records of patients that they treat, but nurses can only access medical records of patients and whose current treating physician is the same physician who the nurse is currently assigned to assist, and only if the nurse I currently badged into the same physical building as the one the patient is located in. As another example, for hospitals and doctors in hospitals, doctors are allowed referrals within the Plan, but doctors not allowed access to patient data outside the US and no bring your own device (BYOD) access allowed outside the US. As shown in FIG. 12, the directive lineage enforcement may be an alert for insurance providers, compliant for hospitals, critical for employees, compliant for patients and critical for partners. In the example in FIG. 12, whether each component (providers, hospitals, patients, employees, etc) is in alignment with the directives or is non-compliant based on their specific activities. The components shown as "Critical" show that, based on the activities in that module, the platform may have identified non-compliant and anomalous activities and flagged that component while the "Alert" flags a component that has some activities which need to be examined Telco Use Case FIG. 13 illustrates a telco security policy enforcement use case that provides security policy enforcement at the edge of the system with its resources. This figure shows similar status for directive alignment in a computer network example with different components have the different statuses generated by the DALE system for each of the components in this example including Public cloud/private cloud/Multi Access Edge Computer and the end points. The use case is about managing the directives centrally and executing them across the stack including the end points/edge. The directives may be different for different system components in the hierarchy as well as combination of multiple directives to be enforced across the different system components Sourcing/Procurement Use Case FIG. 14 illustrates a sourcing/procurement use case whose directives were described above in more detail. In this use case, the system may be used to control access to data and workflows for sourcing and procurement. FIG. 14 also shows examples of the policy updates that may be done based scenario modeling.

The foregoing description, for purpose of explanation, has been with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include and/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general-purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software, and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

What is claimed is:

1. A system, comprising:
   a plurality of entities interacting with each other and with a resource, a set of access actions for each entity to access the resource being controlled by a directive, the plurality of entities having a lineage with a primary node for a primary entity and one or more sub-nodes for one or more sub-entities underneath the primary node wherein a directive for the primary node flows downstream to the one or more subnodes and affects the access to the resource by the one or more subnodes;
   a computer based directive based access lineage control system having a processor and memory that is connected to each of the one or more entities to manage and control the access to the resource by the each of the one or more entities;
   the computer based directive based access control system having a plurality of lines of instructions executed by the processor that configures the processor to implement a directive access lineage engine that manages and controls the access to the resource by each entity based on the directive for each entity and the lineage and synchronize one of a new directive and an updated directive to each entity.

2. The system of claim 1, wherein the processor is further configured to, using the directive access lineage engine, map a behavior of the entity relative to the directive for access to the resource to determine if the entity is in alignment with the directive.

3. The system of claim 1 further comprising a directive access dictionary associated with the computer based directive based access control system that stores the directive for each entity including the new directive and the updated directive.

4. The system of claim 1, wherein the processor is further configured to automatically update the directive to generate the updated directive that modifies an access right of the entity to the resource.

5. The system of claim 1, wherein the directive further comprises a plurality of access actions and access limits for access to the resource by the entity.

6. The system of claim 5, wherein the directive is one of an organizational directive, a regulatory directive, a customer directive and a resource directive.

7. The system of claim 1, wherein the resource is patient health data and the one or more entities are a doctor, a nurse, a hospital and a third party system wherein access to the patient health data is controlled by the directive based access lineage control system.

8. The system of claim 1, wherein the resource is an asset and the one or more entities are cloud computer systems wherein access to the asset is controlled by the directive based access lineage control system.

9. The system of claim 1, wherein the resource is workflow data and the one or more entities are a system wherein access to the workflow data is controlled by the directive based access lineage control system.

10. A system, comprising:
    a plurality of entities interacting with each other and with a resource, a set of access actions for each entity to access the resource being controlled by a directive, the plurality of entities having a lineage with a primary node for a primary entity and one or more sub-nodes for one or more sub-entities underneath the primary node wherein a directive for the primary node flows downstream to the one or more subnodes and affects the access to the resource by the one or more subnodes;
    a computer based directive based access lineage control system having a processor and memory that is connected to each of the one or more entities to manage and control the access to the resource by the each of the one or more entities;
    the computer based directive based access control system having a plurality of lines of instructions executed by the processor that configures the processor to implement a directive access lineage engine that manages and controls the access to the resource by each entity based on the directive for each entity and the lineage and to determine if a request for access by the entity to the resource is permitted based on the directive associated with the entity.

11. A directive based access control method, the method comprising:
    receiving, by a computer based directive access control system from an entity, a request for access to a resource;
    obtaining, from a directive access dictionary of the computer based directive access control system, a directive for the entity that controls access to the resource;
    determining, by the computer based directive access control system, a lineage that may affect the access by the entity to the resource, the lineage including a primary node for a primary entity and one or more sub-nodes for one or more sub-entities underneath the primary node wherein a directive for the primary node flows downstream to the one or more subnodes and affects the access to the resource by the one or more subnodes; and
    determining whether access to the resource is permitted by the entity based on the obtained directive and the lineage for the access to the resource, wherein the directive further comprises a plurality of access actions and access limits for access to the resource by the entity.

12. The method of claim 11 further comprising synchronizing one of a new directive and an updated directive to each entity.

13. The method of claim 12 further comprising automatically updating, by the computer based directive access control system, the directive to generate the updated directive that modifies an access right of the entity to the resource.

14. The method of claim 11 further comprising mapping a behavior of the entity relative to the directive for access to the resource to determine if the entity is in alignment with the directive.

15. The method of claim 11, wherein the directive is one of an organizational directive, a regulatory directive, a customer directive and a resource directive.

16. The method of claim 11, wherein the resource is patient health data and the one or more entities are a doctor, a nurse, a hospital and a third party system wherein access to the patient health data is controlled by the directive based access lineage control system.

17. The method of claim 11, wherein the resource is an asset and the one or more entities are cloud computer systems wherein access to the asset is controlled by the directive based access lineage control system.

18. The method of claim 11, wherein the resource is workflow data and the one or more entities are a system wherein access to the workflow data is controlled by the directive based access lineage control system.

\* \* \* \* \*